(12) United States Patent
Buchholz et al.

(10) Patent No.: US 7,041,652 B1
(45) Date of Patent: May 9, 2006

(54) ASCORBATE-ISOQUERCETIN COMPOSITIONS

(75) Inventors: Herwig Buchholz, Frankfurt (DE); Jerzy Meduski, Playa del Rey, CA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/763,602

(22) PCT Filed: Aug. 23, 1999

(86) PCT No.: PCT/EP99/06166

§ 371 (c)(1),
(2), (4) Date: Jun. 7, 2001

(87) PCT Pub. No.: WO00/12085

PCT Pub. Date: Mar. 9, 2000

(51) Int. Cl.
*A61K 31/70* (2006.01)
*A61K 31/34* (2006.01)

(52) U.S. Cl. .................................. 514/25; 514/474
(58) Field of Classification Search ............. 514/474, 514/25
See application file for complete search history.

(56) References Cited

U.S. PATENT DOCUMENTS 5,830,914 A    11/1998    Kimoto et al.

FOREIGN PATENT DOCUMENTS

| | | |
|---|---|---|
| DE | 19820680 | 9/1999 |
| EP | 0954986 | 11/1999 |
| JP | 04099771 | 3/1992 |
| JP | 06199692 A | 3/1992 |
| JP | 6199690 | 7/1994 |
| JP | 6199693 | 7/1994 |
| JP | 7196523 | 8/1995 |
| JP | 9030987 | 2/1997 |

OTHER PUBLICATIONS

Seto T et al "Purgative Activity and Pricipals of the Fruits of Rosa multiflora and R. wichuraina" Chem. Pharm. Bull. vol. 40 No. 8, 1992 p. 2080-2082.
Database WPI Section Ch, Week 199433 Derwent Publications Class B05, AN 1994-269369.
Database WPI Section Ch, Week 199433 Derwent Publications Class B05, AN 1994-269367.
Database WPI Section Ch Week 199715 Derwent Publications Class A96, AN 1997-161434.
Database WPI Section Ch, Week 199539 Derwent Publications Class B02, AN 1995-299503.
Noroozi M et al "Effects of Flavonoids and Vitamin C on oxidative DNA damage to Human Lymphocytes" American Journal of Clinical Nutrition, vol. 67, 1998 p. 1210-1218.
Vrijsen R et al "Antiviral Activity of Flavones and Potentation by Ascorbate" Journal of General Virology, vol. 69, 1988 p. 1749-1751.

*Primary Examiner*—Zohreh Fay
(74) *Attorney, Agent, or Firm*—Millen, White, Zelano & Branigan, P.C.

(57) ABSTRACT

The present invention relates to novel compositions containing ascorbic acid with an increased bioavailability of this vitamin. These compositions are useful as food supplements possessing preventive properties against damages of human organs, including skin, tissues and cells due to oxidative stress or damages.

10 Claims, No Drawings

ASCORBATE-ISOQUERCETIN COMPOSITIONS

The present invention relates to novel compositions containing ascorbic acid with an increased level of its active form. These compositions are useful as food supplements possessing preventive properties against damages of human tissues, including skin cells due to oxidative stress.

In vivo ascorbic acid (vitamin C) exists in three forms:

a) as an ascorbate in form of an ascorbate monoanion, b) as the reversibly oxidised form of a free radical, called semidehydroascorbic acid which could be reversibly oxidised to dehydroascorbic acid or reversibly reduced to ascorbate monoanion, and c) as dehydroascorbic acid (oxidised form of semidehydroascorbic acid).

Only ascorbate possesses specific vitamin C activity: as a cofactor for enzymes. Observed physiological activities of semidehydroascorbic acid and dehydroascorbic acid formed in vivo from ascorbate are considered to be based on their reversible reductions to ascorbates, (Buettner, 1993—Dharival et al., 1991; Welch et al., 1995 Washko et al., 1993). The second form of ascorbic acid, semidehydroascorbic acid (ascorbate free radical) participates in univalent redox systems, (Bors et al. 1995), that is in the antioxidant defence activity. This means, semidehydroascorbic acid participates most likely in free radical scavenging activities. According to Gordon (1996, p. 270), "ascorbate appears to be the most important non-protein antioxidant in plasma". Ascorbic acid is absorbed from the gastrointestinal tract in the form of ascorbic acid. Dehydroascorbic acid is reduced to ascorbic acid for gastrointestinal absorptions (Rose et al., 1988).

Structures of body tissues are susceptible to damages caused by the oxidative stress, e.g. by the accumulation of reactive oxygen species during ageing, chronic environmental stress, inflammations or general metabolic dysfunctions. The role of free radicals and reactive oxygen species in aetiology of human diseases (e.g. cancer, atherosclerosis, rheumatoid arthritis, inflammatory bowel diseases, immune system dysfunctions, brain function decline, connective tissue dysfunctions) is well established (for a recent review see: Gordon, 1996). Uncontrolled generation of free radicals, especially chronic exposure to reactive oxygen species leads to chronic intracellular damages, to oxidative stress and premature ageing. Cells of the human body possess metabolic antioxidant defences which are supported by dietary antioxidants. The early observations of the antioxidant defence metabolic processes involved vitamin C and flavonoids (Bezssonoff, 1926; Bentsath et al., 1936; Bensath et al., 1937; Blanc and Von der Muehl, 1967). Ascorbic acid is not only important non-protein antioxidant in human plasma (Gordon, 1.c.) but it increases (Skaper et. al., 1997) the cytoprotective activities of quercetin and rutin. Skaper and co-authors (1997) have shown, for instance, that quercetin protects connective tissue and specifically skin cells (e.g. fibroblasts, keratinocytes, and endothelial cells) from this type of damages. Other authors have demonstrated protective effect of flavonols on cardiovascular and nervous system, their role as chemoprotective agents in carcinogenesis.

Oxidation of the ascorbate in the human body by xenobiotics often leads to the accumulation of semidehydroascorbic acid or dehydroascorbic acid in organs where these forms interfere with the regular metabolism. As ascorbate is a cofactor for eight isolated enzymes (carrying out collagen synthesis, carnitine synthesis, peptide amidation, tyrosine metabolism, and catecholamine synthesis) the decrease of the concentration of ascorbate in body tissues and fluids may leads to serious metabolic dysfunctions.

The possibilities to protect ascorbic acid in vivo were based on very early observations of Szent-Györgyi group mentioned above that the ascorbic acid activity in humans and guinea pigs is intensified by the great group of "vegetable dyes, the flavons or flavonols". It has been known that flavonoids are contributing to the maintenance of the concentration of the administered ascorbate in adrenals, kidneys, spleen, and the liver of the organisms investigated and improve the antiscorbutic effect of the dosages of ascorbate used (Papageorge and Mitchell, 1948; Cotereau et al., 1948; Crampton and Lloyd, 1950; Douglas and Kamp, 1959; Blanc and Von der Muehl, 1967; Zloch, 1973).

The mechanism of this effect, called "the vitamin C-economising function" of some flavonoids ("facteur d'economie de L'acide ascorbique" of Bezssonoff, 1926 and 1927) has been recognised in many laboratories. For example, Harper et al., 1969, found that, among flavonoids tested, flavonols the have strongest ability to inhibit ascorbic acid oxidation in near neutral solutions (pH 5–7). Harper et al. (1.c.) also pointed out that the presence of free hydroxyl groups at carbon atoms-3, 7, 3', and 4' in a flavonol molecule improves the antioxidative effect of the flavonol molecule, this means, it inhibits ascorbate oxidation more effectively.

But there was neither an effective method nor a useful orally applicable formulation leading to an increased level of active ascorbate in human tissue.

Accordingly, there was a need for a composition useful for the protection of the orally administered ascorbic acid and enhancement of vitamin activity in the tissues.

Now it has been found that isoquercetin effectively inhibits ascorbate oxidation. The maintenance of the reduced form of ascorbic acid by isoquercetin maintains ascorbic acid level in body tissues and fluids.

This effect perhaps may be explained in that isoquercetin not only shows three free hydroxyl groups mentioned by Harper (1.c.), more exactly, hydroxyl groups attached to carbon atoms 7, 3', and 4', but also a glucopyranoside moiety with additional four free hydroxyl groups 0-attached to the carbon 3 of isoquercetin. Therefore, the increased effectivity of ascorbate protectioin may be caused by the fact that isoquercetin contains a glucose molecule. This glucose molecule seems to be the reason why isoquercetin is able to use the sodium-dependent glucose transport pathway of the intestinal brush-border membrane in its absorption process (Gee et al., 1998). Experiments have also shown that the absorption of isoquercetin is better than that of pure aglycone.

Earlier pharmacokinetic studies with isoquercetin anticipated results obtained and explained by Gee at al,. 1.c., by having shown excellent absorption rate and bioavailability of isoquercetin (Hollman and Katan, 1997).

It has been found that ascorbate is not only able to regenerate oxidised flavonols by reducing them (Yamasaki et al., 1997) but also to protect quercetin (aglycone of the isoquercetin) against oxidative degradation and to maintain the antiviral properties of quercetins (Vrijsen et al., 1988).

This means, there is a synergistic effect between isoquercetin and ascorbate in human tissue leading to higher effectivities of both, ascorbate and isoquercetin.

For isoquercetin these activities are as follows:

it has shown anthypertensive properties, (Kameda et al., 1987); it inhibits the biosynthesis and release of prostaglandin-like substances (Chanh et al. 1986); it produces dose-dependent protection in oxidative DNA damage Noroozi et al., 1998), it possesses preventive properties against damages of vascular and connective tissues (especially skin) and it is therapeutically useful in the treatment of dysfunctions of the digestive tract (Seto et al. 1992).

Now we have found by experiments that the combination of vitamin C with the most easily bioavailable bioflavonoid, isoquercetin, is most effective in prevention of and in defense against stress dysfunctions, especially against oxidative damages of living tissues including brain, vascular, connective tissues (especially skin).

It has been found that a composition containing ascorbic acid and one or more derivates of quercetin elected from the group quercetin-3-O-glucoside (isoquercetin), quercetin-4'-glucoside, quercetin-3'-glucoside and acid-quercetin-7-glucoside in a molar ratio of ascorbate to flavonoid in the range of 2:1 to 1:2, preferably in the molar ratio of 1:1, orally administered conveys in vivo higher protection, longer maintenance of biological activity, higher concentration in tissues and higher biological efficiency to vitamin C in organs of human body. This adduct similarly also provides the properties of higher protection, longer maintenance of biological activity, higher concentration in tissues, and higher biological efficiency in organs of human body to isoquercetin and the other glucosides of the above mentioned groups.

Useful compositions may contain in a daily dose 30–4000 mg of an active amount of ascorbic acid or preferably of physiologically active ascorbate in form of its sodium salt, calcium, other mineral, or organic cation salts. Usually compositions contain 150–1000 mg, but for special treatments the amount is chosen higher between 1000 and 4000 mg, preferably between 1500 and 3000 mg. The compositions according to the present invention may be prepared in form of tablets, capsules or syrups. These application forms may also contain further active ingredients in useful amounts like vitamins, suitable salts of Mg, Ca, K or Fe and perhaps trace elements.

The compositions of the present invention preferably are useful as food supplements, but they may also be administered in a pharmaceutical treatment.

The present invention makes available a) a method of maintaining long biological activity and high concentration of ascorbate and isoquercetin in human organs (including skin), tissues and cells, b) a method of protection against oxidative damages of human organs, tissues, skin cells, c) a method of prevention of arteriosclerosis, cardiovascular diseases, and other damages of vascular tissues, of allergic and inflammatory disorders, of bacterial and viral infections, of metabolic dysfunctions involving oxidative damages e.g., premature ageing, d) a method of supporting pharmacological treatments of diseases and dysfunctions caused by oxidative damages, by orally administration of a composition described above. Generally speaking, compositions that are applicable contain at least ascorbic acid or ascorbate or any other form of this vitamin that would in vivo yield ascorbate, or semihydroascorbic acid, or dehydroascorbic acid and isoquercetin. The decision which further ingredients should be components of a composition useful in one of the above mentioned methods depends on the special indication. Usually, if the composition is administered as a way of protection or prevention useful further ingredients may be further vitamins, salts of Mg, Ca, K, Fe and trace elements in known amounts as used in food supplements. Compositions useful in method of supporting pharmacological treatments may differ from them.

The superiority of isoquercetin and ascorbate used in combination for the protection of human cells, tissues and organs from the oxidative stress is based on two properties of isoquercetin and of ascorbate. First, on the quick intestinal absorption of orally administered isoquercetin and of ascorbate, and on the rapid and simple passage of both compounds through cytomembranes of human organs; secondly, on the specificity of interaction of isoquercetin with ascorbate. Specifically, ascorbate maintains isoquercetin in its active oxidised state and isoquercetin maintains ascorbate in its enzymatically active reduced state.

On the basis of our research on the bioavailability and on redox properties of isoquercetin and ascorbate it has been found that orally administered mixtures of isoquercetin and ascorbate are most effective in protecting the organs (including skin), tissues, and cells from the chronic intracellular oxidative damages.

The uptake of isoquercetin into the human body is facilitated by the sodium-dependent glucose transport system. This type of transport occurring in most animal species (Coady et al., 1990) is active during the uptake of pyranosides as for example described by Hediger for methyl alpha-D-glucopyranoside (Hediger et al., 1987). The sodium-dependent glucose transport system in mammals was studied in many laboratories. Koepsell and Spangenberg (1994) characterised Na(+)-D-glucose cotransport in the intestine. It is a cotransporting system composed of a set of two subunits: transport-mediating proteins transport-modulating proteins. The first translocates the substrates and the second accelerates the $V_{max}$ of the Transport. The susceptibility of isoquercetin to be transported using the Na(+)-D-glucose cotransport is suggested to be determined by the manner in which a non-glucose moiety is linked to glucose. More information about this is given in a review of Olson and Pessin, 1996. Direct evidence that isoquercetine uses sodium-dependent glucose transport pathway of the intestinal brush-border membranes was obtained by Gee et al., 1998.

Also the uptake of ascorbate by human is caused by a sodium dependent glucose transport system. Interactions between glucose and ascorbate transport activity have been demonstrated in many tissues and cells (Rumsey and Levine, 1998). Apparently ascorbate is absorbed in human intestine by a sodium-dependent active transport system, although in vitro about 10–20% of ascorbic acid moves into cells in the absence of sodium (Kuo et al., 1997). The carrier proteins in the intestinal cell membranes bind and transport the vitamin across the membrane to its intracellular site of action. There are differences in transport kinetics, tissue specificity, $Na^+$-dependence and energy dependence (Rumsey and Levine, 1.c.), but in most cases the transport of ascorbate is $Na^+$-dependent and requires metabolic energy. Kinetic evidence suggests strongly that ascorbate may be transported by the same transporter as glucose and, therefore, by the same transporter as isoquercetin.

Pharmacokinetic studies with isoquercetin support the present invention as they show excellent absorption rate and bioavailability of isoquercetin. It is absorbed better than rutin and quercetin (Hollman, 1997). Absorbed isoquercetin interacts with ascorbate protecting it and, at the same time, is being protected by ascorbate by being kept in the reduced state (Yamasaki et al., 1997). It has also been shown that ascorbate protects quercetin (aglycone of the isoquercetin) against oxidative degradation and maintains quercetin's antiviral properties (Vrijsen et al., 1988). Effectiveness of isoquercetin in interacting with ascorbate is strengthened by the fact that isoquercetin uses the preferential intestinal Na(4+)-D-glucose cotransport discussed above.

Therefore, a most powerful dietary antioxidant composition is prepared using among other ingredients ascorbic acid and isoquercetin. The advantageous properties of these compositions are induced by the synergistic effect of isoquercetin protecting the activity of the orally administered ascorbic acid while maintaining its enzymatically active reduced form, and, on the other side, of ascorbate maintaining isoquercetin in its active oxidised state.

Surprisingly it was found that in contrast to other quercetin glucosides, isoquercetin shows far better absorption rates in human intestinal tract than rutin or the quercetin aglycone and that it acts as a specific and most powerful dietary antioxidant at the same time.

This positive result was unexpected because mixtures of ascorbic acid and quercetin or quercetin glucosides other than isoquercetin were considerably less effective.

Subject of this invention is that in humans the oral administration of a mixture or combination of ascorbic acid and isoquercetin (quercetin-3-O-glucoside); or of any of mixtures of ascorbic acid and quercetin-4'-glucoside; of ascorbic acid and quercetin-3'-glucoside; of ascorbic acid and quercetin-7-glucoside, with a suitable molar ratio, preferably equimolar ratio, of ascorbate to flavonoid, conveys efficient protection against oxidative damages, due to long maintenance of biological activity of each of the ingredients and due to maintenance of high concentration of both ascorbate and isoquercetin in organs, tissues, and cells.

The invention of this application includes especially compositions containing the above mentioned ingredients useful for the prevention and treatment of atherosclerosis and other cardiovascular disorders, certain forms of cancer, allergic and inflammatory disorders, bacterial and viral infections, a number of metabolic dysfunctions, e.g. premature ageing and other pathological conditions that involve oxidative damages.

REFERENCES

Bentsath A, Rusnyak St, Szent-Gyorgyi A (1936). Vitamin nature of flavones. Nature (London), 138, 798.

Bentsath A, Rusznyak St, Szent-Gyorgyi A (1937). Vitamin P. Nature (London), 139, 326–327.

Bezssonoff N (1926). L'effet antiscorbutique est-il du a deux substances differentes? C.r. Acad. Sci., Paris 183, 1309–1310; Bull. Soc. Chim. Biol. (1927), 9, 568–579.

Blanc, B, and Von der Muehl, M., (1967), Interaction d'une flavonbide et vitamine C; son influence sur le poids du cobaye et le contenu en vitamine C de ses organs. Int. Z. VitaminForsch., 37,156–169.

Bors, W., Michel, Ch., Schikora, S., (1995), Interaction of Flavonoids with Ascorbate and Determination of their Univalent Redox Potentials: a Pulse Radiolysis Study. Free Radical Biology and Medicine, vol 19, No. 1, 45–52.

Buettner GR (1993). The pecking order of free radicals and antioxidants: lipid peroxidation, alpha-tocopherol, and ascorbate. Arch. Biochem. Biophys. 300, 535543.

Chanh, P. H., Ifansyyah, N., Chahine, R., Mounayar-Chalfou, A., Gleye, J. and Moulis, C. (1986), Comparative effects of total flavonoids extracted from Ribes nigrum leaves, rutin and isoquercitrin on biosynthesis and release of prostaglandins in the ex vivo rabbit heart. Prostaglandins 1. Med., 22, 295–300.

Coady, M. J., Pajor, A. M., Wright, E. M.,(990), Sequence Homologies between Intestinal and renal Na(+)/glucose cotransporters. Am. J. Physiol. 259, C605–610

Cotereau, H., Gabe M., Gero, E., Parrot, J. L. (1948) Influence of vitamin P (C2). Upon the amount of ascorbic acid in the organs of the guinea pig. Nature, 161, 557–558.

Crampton, E. W. and Lloyd, L. E., (1950), A qualitative estimation of the effect of rutin on the biological potency of vitamin C. J. Nutr., 41, 487–498.

Dhariwal K R, Black C D, Levine M (1991). Semihydroascorbic acid as an intermediate in norepinephrine biosynthesis in chromaffin granules. J. Biol. Chem. 266, 12908–12914.

Douglas, C. D. and Kamp, G. H., (1959), The effect of orally administered rutin on the adrenal ascorbic acid level in guinea pigs., J. Nutr., 67, 531–536.

Gee, J. M., M. S. DuPont, M. J. C. Rhodes, and Ian T. Johnson, (1998) Quercetin glucosides interact with the intestinal glucose transpot pathway. Free Radical Biology and Medicine, 25, (1), 19–25.

Gordon, M. H., (1996). Dietary Antioxidants in Disease Prevention. Natural Product Reports, pp. 265–273.

Harper, K. A., Morton, A. D. and Rolfe, E. J., (1969), Phenolic compounds of black currant juice and their protective effect on ascorbic acid. III Mechanism of ascorbic acid oxidation and its inhibition by flavonoids. J. Food Tech., 4, 255–267)

Hediger, M. A., Coady, M. J. Ikeda, T. S., Wright, E. M. (1987), Expression and Cloning and CDNA Sequencing of the Na(+)/glucose cotransporter, Nature, 330, 379–381.

Hollman, P. Determinants of the absorption of the dietary flavonoid quercitin in man, Proefschrift. 1997. Universiteit Nijmegen.

Kameda, K., Takaku, T., Okuda, H., Kimura, Y., Okuda, T., Hatano T., Agata, 1. And Arichi, S. (1987). Inhibitory effects of various flavonoids isolated from leaves of persimmon on angiotensin-converting enzyme activity. J. Nat. Prod., 50, 680–683.

Koepsell H. and Spangenberg, J. (1994) Function and presumed molecular structure of Na(+)-D- glucose cotransport systems. J. Membr. Biol. 138, (1) 1–11.

Kuo, S.-M., Morehouse, H. F., Lin, C.-P. (1997) Effect of antiproliferative flavonoids on ascorbic acid accumulation in human colon adenocarcinoma cells. Cancer Letters, 11, 131–137

Noroozi, M., W. J. Angerson, M. E. J. Lean, (1998), Effects of flavonoids and vitamin C on oxidative DNA damage to human lymphocytes. American Journal for Clinical Nutrition, 67, 1210–1218.

Olson, A. L. and Pessin, J. E., (1996), Structure, function, and regulation of the mammalian facultative glucose transporter gene family. Annual Rev. of Nutrition, Vol. 16, 235–256.

Papageorge, E. and Mitchell, G. L. (1949) The effect of oral administration of rutin on blood, liver and adrenal ascorbic acid and on liver and adrenal cholesterol in guinea pigs. J. Nutr. 37, 531–540.

Rose, R. C., J. L. Choi, and M. J. Koch, (1988). Intestinal transport and metabolism of oxidized ascorbic acid. Am. J. Physiol., 254, G824–G828.

Rumsey, S. C. and Levine, M. (1998) Absorption, Transport, and disposition of ascorbic acid in humans. Nutritional Biochemistry, 9, 116–130.

Seto, T., Yasuda, 1, and Akiyama, K. (1992), Purgative activity and principals of the fruits of Rosa multiflora and R. wichuraiana. Chem Pharm. Bull, (Tokyo) 40, 2080 2082.

Vrijsen, R., Everaert L., Boeye, A. (1988), Antiviral activity of flavones and potentiation by ascorbate. Journal of General Virology, 69, 1749–1752)

Washko P. W., Wang Y., Levine M. (1993). Ascorbic acid recycling in human neutrophils. J. Biol. Chem. 268, 15531–15535.

Welch R. W., Wang Y., Crossman A. Jr., et al. (1995). Accumulation of vitamin C (ascorbate) and its oxidised metabolite dehydroascorbic acid occurs by separate mechanisms. J. Biol. Chem. 270, 12584–12592.

Yamasaki, H., Sakihama Y., Ikehara, N., (1997), Flavonoid-peroxidase reaction as a detoxification mechanism of plant cells against H2O2, Plant Physiology, 115, 1405 1412)

Zloch, Z.,(1973), Einfluss von Bioflavonoiden auf den Vitamin-C-Wert kristalliner Dehydroascorbinsaeure Int. J. Vit. Nutr. Res. 43, 378–386.

What is claimed is:

1. A method of extending the biological activity lifetime of ascorbic acid, ascorbate or a derivative thereof, comprising administering ascorbic acid, ascorbate or a derivative thereof in combination with one or more of quercetin-3-O-glucoside (isoquercetin), quercetin-4'-glucoside, quercetin-3'-glucoside, or quercetin-7-glucoside, in a molar ratio of from about 2:1 to about 1:2.

2. The method of claim 1, wherein said ascorbic acid or ascorbate is present in an amount ranging from 150 to 1000 mg in a daily dose.

3. A method according to claim 1 wherein said isoquercetin is in combination with ascorbic acid or a physiologically active ascorbate in the form of its sodium, calcium, or other mineral or organic salt.

4. A method according to claim 1 wherein said isoquercetin is in combination with ascorbic acid or a mineral or organic salt thereof.

5. A method according to claim 1 wherein said combination further comprises a vitamin.

6. A method according to claim 1 wherein said combination further comprises a Mg, Ca, K, or Fe salt.

7. A method according to claim 1 wherein said combination further comprises a trace element.

8. A method according to claim 1 wherein said combination of ascorbic acid or ascorbate and isoquercetin is in a molar ratio of about 1:1.

9. A method according to claim 1 wherein said ascorbic acid or ascorbate is present in an amount ranging from 30 to 4000 mg in a daily dose.

10. A method according to claim 1 wherein said ascorbic acid or ascorbate is present in an amount ranging from 1500 to 3000 mg in a daily dose.

* * * * *